United States Patent [19]
Forsmalm et al.

[11] Patent Number: 5,584,694
[45] Date of Patent: Dec. 17, 1996

[54] METHOD FOR IMPRESSION-TAKING AND FOR PRODUCTION OF DENTAL PROSTHESES ANCHORED IN THE JAWBONE

[75] Inventors: Göran Forsmalm, Frölunda; Torsten Jemt, Lerum; Lars Jornéus, Frillesås, all of Sweden

[73] Assignee: Nobelpharma AB, Goteborg, Sweden

[21] Appl. No.: 296,804

[22] Filed: Aug. 26, 1994

[30] Foreign Application Priority Data

Aug. 26, 1993 [SE] Sweden .................................. 9302760

[51] Int. Cl.⁶ ........................ A61C 13/12; A61C 13/225; A61C 9/00
[52] U.S. Cl. .............................................. 433/172; 433/214
[58] Field of Search .................................. 433/172, 173, 433/174, 175, 176, 213, 214

[56] References Cited

U.S. PATENT DOCUMENTS

| | | | |
|---|---|---|---|
| 4,708,654 | 11/1987 | Branemark | 433/213 |
| 4,854,872 | 8/1989 | Detsch | 433/174 X |
| 4,906,191 | 3/1990 | Soderberg | 433/213 |
| 4,955,811 | 9/1990 | Lazzara et al. | 433/213 X |
| 5,125,833 | 6/1992 | Berceaux | 433/213 X |
| 5,135,395 | 8/1992 | Marlin | 433/174 |
| 5,145,371 | 9/1992 | Jorneus | 433/173 |
| 5,195,890 | 3/1993 | Johansson et al. | 433/213 X |
| 5,213,502 | 5/1993 | Daftary | 433/214 X |

*Primary Examiner*—Nicholas D. Lucchesi
*Attorney, Agent, or Firm*—Pollock, Vande, Sande & Priddy

[57] ABSTRACT

This method increases the precision of the components in an impression system for dental prosthesis of the type permanently anchored in the jaw by at least one securing elements implanted in the jawbone. Each of the securing elements is provided with a distance member whose upper part protrudes above the palatal arch and on which the finished dental bridge/dental prosthesis is then anchored via a so-called gold cylinder. The system includes impression components in the form of impression tops and distance dummies with continuous guide holes and stop members for a guide pin which, during fixing of the components, is guided through the respective guide hole and engages with the stop members of the respective impression component. That part of the guide pin which interacts with the stop members of the guide holes of the respective impression component has a conical stop surface, while the stop members form plane surfaces and guide edges. By such a design of the guide pin, the components are centered and the precision is improved in existing impression systems.

10 Claims, 3 Drawing Sheets

5,584,694

METHOD FOR IMPRESSION-TAKING AND FOR PRODUCTION OF DENTAL PROSTHESES ANCHORED IN THE JAWBONE

FIELD OF THE INVENTION

The present invention relates to a method for increasing the precision of impression-taking and production of dental prostheses of the type permanently anchored in the jaw by means of one or more securing elements implanted in the jawbone. Each of these securing elements is provided with a distance member whose upper part protrudes above the palatal arch and on which the finished dental prosthesis/dental bridge is then anchored via a so-called gold cylinder.

BACKGROUND OF THE INVENTION

Dental bridges which are so anchored on distance members must be carefully adapted to the actual appearance of the jaw. The way in which this can be done is shown, for example, in Swedish Patent 446371 which describes how a positive working model of a lower or upper jaw provided with protruding distance members of this type can be produced. The impression system which is used there includes components such as impression tops and distance dummies which are fixed with the aid of guide pins.

A positive working model of the jaw obtained in this way is used by the dental technician for producing the finished dental prosthesis/dental bridge so that he does not have to carry out the time-consuming and complicated work involved in adapting the prosthesis directly in the patient's mouth. Instead, he works with a model of the patient's jaw. The production of the positive working model is facilitated with the aid of the components included in the impression system, namely the impression tops, distance dummies, gold cylinders and guide pins. It is known in the art how the various impression components are used and will therefore not be described in detail here. However, it will be noted that the impression technique and the production of the model comprise four stages:

the impression top is placed on the distance member,
 the distance dummy is placed on the impression top,
 the impression top is placed on the gold cylinder,
 the gold cylinder is placed on the distance member.

In the first three stages a guide pin is used to fix the components to each other, while the gold cylinder is fixed on the distance member with the aid of a gold screw. Since the components always have a certain tolerance deficit, a degree of error is introduced during each of the four stages. The errors add up and can lead to stresses being built into the finished dental bridge.

To be more specific, the tolerance deficit results in the center of the various components ending up eccentric upon assembly. A guide pin is used which can facilitate centering, but the guide pin which has hitherto been used has a plane stop surface or contact surface which interacts with corresponding plane stop surfaces and guide edges of the respective component. Such a system gives a correct transfer vertically, but a certain error laterally since there is always a built-in play between the guide edge and guide bevel of the components.

It has also been proposed to make conical surfaces interact in an impression system, that is, to use a guide pin with conical guide surface which can interact with conical stop surfaces of the various components. Such a system should give a correct lateral positioning on account of the centering capacity of the guide pin, but it has hitherto required a new set of components with conical guide holes.

SUMMARY OF THE INVENTION

The object of this invention is to remedy the shortcomings and disadvantages which are found in the earlier impression methods and to compensate for sources of error in the impression method and in the fitting of the finished dental bridge in the mouth. According to the present invention, this is achieved by providing that part of the guide pin which interacts with the stop members of the guide holes of the respective impression component with a conical stop surface, while the stop members of the impression components form plane surfaces and guide edges.

By means of the conical stop surface, the centering capacity of the guide pin increases and at the same time the interacting plane surfaces and guide edges of the guide holes of the impression components ensure, on the one hand, that the vertical precision is maintained and, on the other hand, that a certain desirable and controlled lateral play can be maintained, for example for the gold cylinder, when compared with the situation in an earlier model where these surfaces would also have been conical.

In order to further improve the precision, the method also involves minimizing the play between distance member and impression top and between impression top and distance dummy, while an intentional and adapted play is allowed between gold cylinder and distance member.

An exemplary embodiment of the invention is described hereinbelow with reference to the attached drawings, in which

DETAILED DESCRIPTION OF THE PREFERRED EMBODIMENT

Figure 1A:
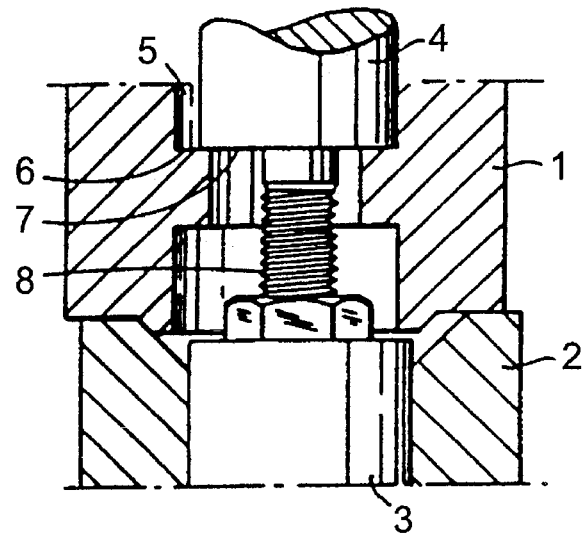
FIGS. 1a–1c show diagrammatically, various stages during impression-taking in accordance with a known prior art technique.

FIG. 1a shows the first stage in the impression technique, namely the positioning of an impression top 1 on a distance member 2. The distance member is fitted in a known manner on a securing element (not shown) by means of a distance screw 3. The impression top I is secured on the distance member 2 with the aid of a guide pin 4, and the impression top therefore has a continuous guide hole 5 for the guide pin. The diameter of the guide hole is slightly larger than the diameter of the guide pin. A stop 6 is arranged in the guide hole, which interacts with a flat stop part 7 of the guide pin. The guide pin is additionally provided with a lower, narrower, threaded part 8 which is screwed firmly into a corresponding threaded hole in the distance screw 3. The flat guide pin, when it is tightened, gives only a compressive force which acts on the component which is to be firmly screwed. The direction of the compressive force is axial, which means that the component will not move in the radial direction. The guide pin with the flat stop surface does not therefore have any centering capacity with respect to the play which is always present between the guide pin and the guide hole. This play or clearance can amount to about 0.1 to 0.2 mm, and a corresponding error is already built into the impression system at this first stage.

Figure 1B:
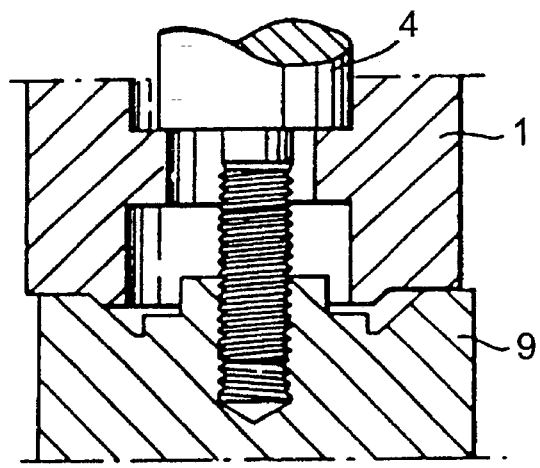

FIG. 1b shows stage 2 in which a distance dummy 9 is fitted on the impression top 1. The guide pin 4 is also used here for securing the two components to each other. On account of the unavoidable play between the guide pin and the guide hole in the impression top, a new error is added to the one already existing in the impression technique.

Figure 1C:
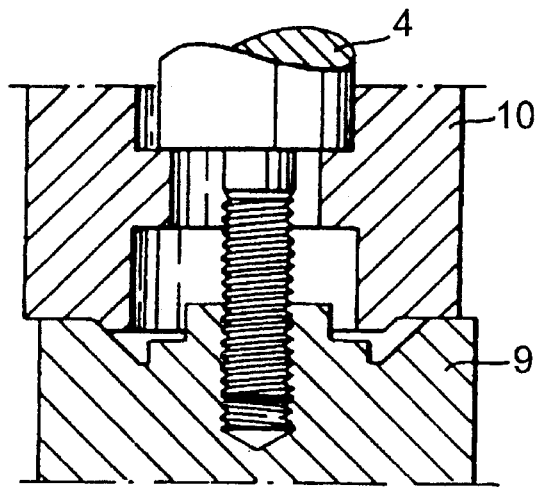

FIG. 1c shows a further stage in the impression-taking, namely when the gold cylinder 10 is connected to the distance dummy 9. A further centering error is added here to the two earlier ones.

Figure 2A:
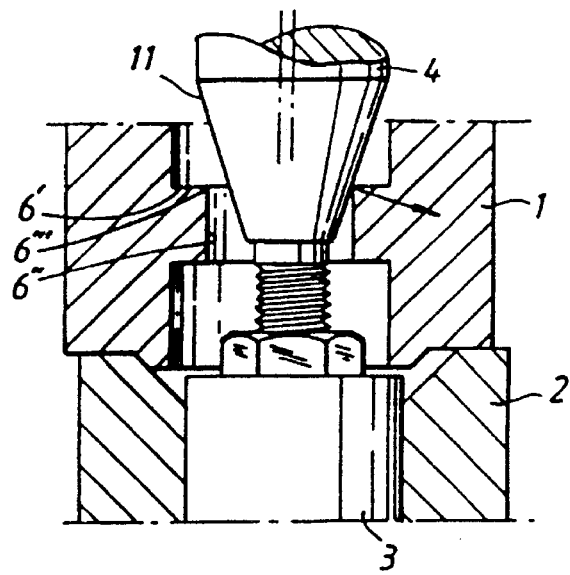
FIGS. 2a–2c show corresponding stages using a method according to the present invention.
Figure 2B:
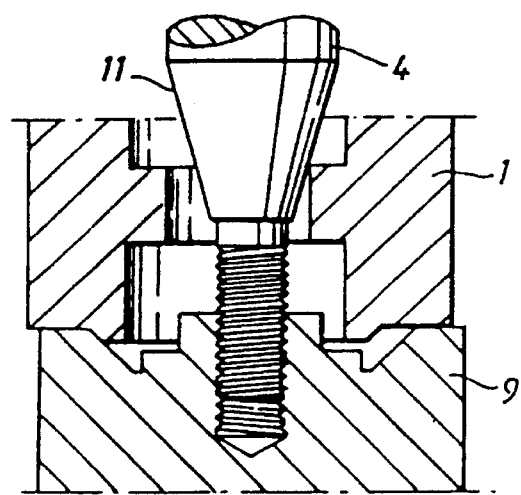
Figure 2C:
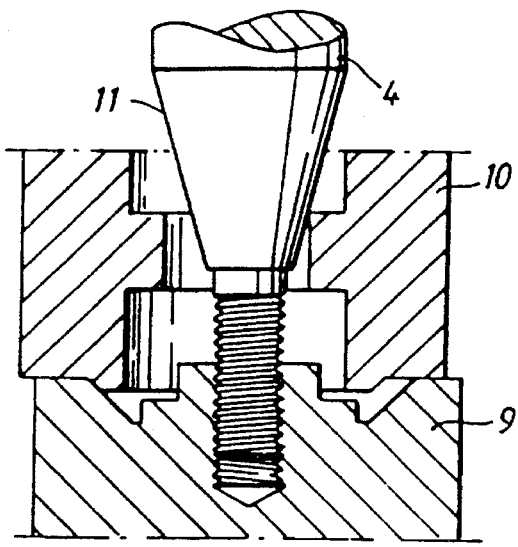

FIG. 2 shows corresponding stages in the impression/model production, but using the new technique according to the present invention. Also in this case the impression components, that is, impression top 1, distance dummy 9 and gold cylinder 10, are provided with stops 6 having plane surfaces and guide edges, that is a horizontal annular surface 6' and a cylindrical surface 6", while the guide pin has a conical stop surface 11 which interacts with the edge 6''' of the stop 6. As the guide pin is screwed firmly into the distance member or the distance dummy, this means that the contact force (P) will act at right angles with respect to the contact surface 11. The contact force can be divided up into two force components one which acts in the axial direction (N) and one which acts in the radial direction (F). The radial force component can displace the component in this plane if cone angle and friction coefficient are favorable.

Figure 3:
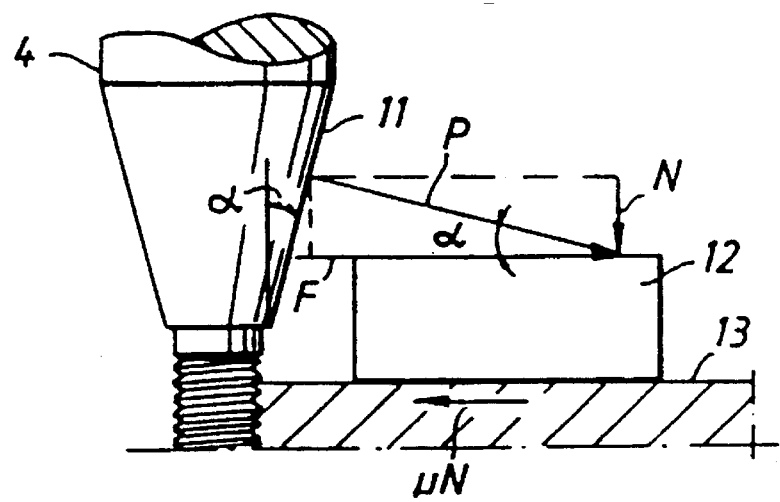
FIG. 3 shows a model for calculating the cone angle of the guide pin.

How the cone angle α of the guide pin 4 can be calculated is shown in FIG. 3. In the figure, the contact surface 11 of the guide pin is assumed to interact with a body 12 which can be displaced along a plane 13. Just as the body begins to slide, it is affected by the friction force $\mu N$. Experiments have shown that the friction coefficient $\mu$ lies within the range of $0.23<\mu<0.55$ depending on the material combination in the contact surface.

From FIG. 3 it follows that $$F=\mu N$$

$$\tan \alpha = N/F$$

which yields $$\tan \alpha = 1/\mu$$

for $\mu=0.23$ it follows that $\alpha \leq 77°$ and $2\alpha \leq 154°$
for $\mu=0.55$ it follows that $\alpha \leq 61°$ and $2\alpha \leq 122°$.

Twice the cone angle should therefore be smaller than 120° in order to allow for the component to be able displacement. Twice the cone angle should expediently lie within the range $15° \leq 2\alpha \leq 90°$ since the friction coefficient just before the component begins to slide (start friction) is greater than the sliding friction. The lower limit of 15° is chosen so that the guide pin will not jam.

As a result of the centering capacity of the conical guide pin, the precision in the first three stages of the impression method is therefore increased. In the fourth and final stage, when the gold cylinder is placed on the distance member, a flat gold screw is used instead of the conical guide pin, since a certain play is desirable between gold cylinder and distance member (see below).

The tolerances of the components which are used in the impression system will be chosen with regard to two factors:

the impression components will be able to perform their function in a satisfactory manner, it will be possible for the components to be manufactured at a moderate cost.

As regards the function of the components, the tolerance ranges for distance member, impression top, distance dummy and gold cylinder will be as "small" as possible. This is particularly important for the first three components, since "small" and correctly placed tolerance ranges result in a lower possible play between the components during the impression procedure.

Figure 4:
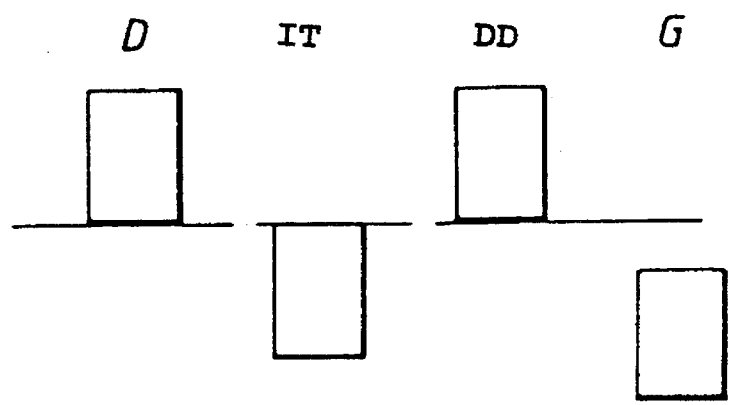
FIG. 4 illustrates the relation between the tolerance ranges of the various components.

FIG. 4 illustrates, diagrammatically, tolerance ranges for the components, namely distance member (D), impression top (IT), distance dummy (DD) and gold cylinder (G). For the first three components mentioned, the tolerance ranges should lie edge to edge, as is shown in the figure, so that the "worst" tolerance deficit will be as small as possible and so that the components will always fit each other.

In contrast, the tolerance range for the gold cylinder (G) will be placed in such a way that there is always a certain play with respect to the distance member. This predetermined and intentional play will allow to fit a dental bridge in the mouth cavity even if there is a certain error in relation to the positioning of the distance members in the mouth cavity. The intentional play between gold cylinder (G) and distance member (D) is preferably within the range of 0.05–0.2 mm.

The optimized tolerance, in combination with the guide pin formed with a conical stop surface, thus minimizes error in the lateral (xy) direction in the production of a model and bridge. Residual error in this direction is then compensated by an intentional and calculated play between gold cylinder and distance member in combination with a non-centering screw connection (gold cylinder/flat gold screw) when the construction is finally anchored in the patient's mouth.

We claim:

1. An apparatus for increasing the precision of an impression system for dental prosthesis of the type permanently anchored in the jaw by means of at least one securing element implanted in the jawbone, through a distance member whose upper part protrudes above a palatal arch and on which the finished dental prothesis/dental bridge is then anchored via a cylinder member, comprising:

at least one impression component comprised of an impression top, a distance dummy, a guide pin extendable through a guide hole of said distance dummy, and a stop member, a conical stop surface on said guide pin, and a plane surface and a guide edge on said stop member, wherein upon insertion of said guide pin through said guide hole, said conical stop surface engages said stop member and thus aligns said impression component.

2. An apparatus according to claim 1, wherein said conical stop surface of said guide pin has twice a cone angle $2\alpha$ within the range of $15° \leq 2\alpha \leq 90°$.

3. An apparatus according to claim 1, wherein said guide pin when inserted minimizes play between said distance member and said impression top and between said impression top and said distance dummy, but allows an intentional and adapted play between said cylinder member and said distance member.

4. An apparatus according to claim 3, wherein said intentional play present between said cylinder member and said distance member is within the range of 0.05–0.2 mm.

5. An apparatus according to claim 2 wherein said distance member, said impression top, said distance dummy and said cylinder member have minimized tolerance ranges which are formed edge-to-edge with each other, and said tolerance range of said cylinder member has an adapted play in relation to said distance member.

6. A method for increasing the precision of an impression system for dental prostheses of the type permanently anchored in the jaw by means of at least one securing element implanted in the jawbone, through a distance member whose upper part protrudes above the palatal arch and on which a finished dental prothesis/dental bridge is then anchored via a cylinder member, said method including the steps of:

provided impression components including an impression top, a distance dummy, a stop member, and a guide pin extendable through a guide hole of said distance dummy, providing a conical stop surface on said guide pin, providing a plane surface and a guide edge on said stop member, inserting said guide pin through said guide hole so that said conical stop surface engages said stop member and thus aligns said impression component.

7. A method according to claim 6, wherein said conical stop surface of said guide pin has twice a cone angle $2\alpha$ within the range of $15° \leq 2\alpha \leq 90°$.

8. A method according to claim 6 wherein insertion of said guide pin minimizes play at least between said distance member and said impression top, but allows an intentional and adapted play between said cylinder member and said distance member.

9. A method according to claim 8 wherein said intentional play is within the range of 0.05–0.2 mm.

10. A method according to claim 8 further including the steps of:

forming tolerance ranges of said distance member, said impression top and said distance dummy edge-to-edge with each other, and forming said tolerance range of said cylinder member so that it has adapted play in relation to said distance member.

* * * * *